US005320834A

United States Patent [19]

Ounanian et al.

[11] Patent Number: 5,320,834
[45] Date of Patent: Jun. 14, 1994

[54] INVISIBLE FOUNDATION COMPOSITION

[75] Inventors: Hovic O. Ounanian, Princeton Junction, N.J.; Natividad R. Jose, Jamaica, N.Y.; Joseph DiSomma, Ramsey; Harvey Gedeon, Allendale, both of N.J.

[73] Assignee: The Procter & Gamble Company, Cincinnati, Ohio

[21] Appl. No.: 39,550

[22] Filed: Mar. 29, 1993

Related U.S. Application Data

[63] Continuation of Ser. No. 736,592, Jun. 12, 1991, abandoned, which is a continuation of Ser. No. 441,305, Nov. 27, 1989, abandoned.

[51] Int. Cl.$^5$ ............................................. A61K 7/021
[52] U.S. Cl. ...................................... 424/63; 424/64; 424/70; 424/401
[58] Field of Search ...................... 424/63, 64, 70, 401

[56] References Cited

U.S. PATENT DOCUMENTS

| 4,659,562 | 4/1987 | Arraudeau | 424/64 |
| 4,837,011 | 6/1989 | Macchio | 424/63 |
| 5,035,890 | 7/1991 | Braun | 424/63 |
| 5,039,518 | 8/1991 | Barone | 424/63 |
| 5,061,481 | 10/1991 | Suzuki | 424/63 |

FOREIGN PATENT DOCUMENTS 2228477 8/1990 United Kingdom .

*Primary Examiner*—Thurman K. Page
*Assistant Examiner*—W. Benston
*Attorney, Agent, or Firm*—John M. Howell; Steven J. Goldstein; Michael E. Hilton

[57] ABSTRACT

An improved foundation composition for application to the skin is disclosed. The composition is characterized by the inclusion of a light scattering agent having a spherical shape and a diameter of up to 30 microns. This component permits the non-inclusion of a colorant. The absence of a colorant allows the foundation composition to be invisible on the skin.

7 Claims, No Drawings

INVISIBLE FOUNDATION COMPOSITION

This is a continuation of application Ser. No. 07/736,592 filed on Jun. 12, 1991, abandoned, which is a continuation of Ser. No. 07/441,305 filed on Nov. 27, 1989, now abandoned.

BACKGROUND OF THE DISCLOSURE

1. Field of the Invention

In a program of beauty enhancement a foundation composition is applied to the face and other parts of the body to even skin tone and texture and to hide pores, imperfections, fine lines and the like. A foundation composition is also applied to moisturize the skin, to balance the oil level of the skin and to provide protection against the adverse effects of sunlight, wind and the harsh environment.

In spite of these positive results, foundation compositions have been criticized because of their unpleasant feel and, more importantly, for their coloring of the skin. Since they provide color, the user must select a shade that suits the user's complexion and coloring. Not only is this a difficult and subjective decision but it is made at the point of purchase. The place of purchase oftentimes has lighting that differs from the lighting at other places. Moreover, lighting changes during the day. Therefore, proper foundation coloring needs continually vary. The constraint of a single shade, imposed by the foundation compositions of the prior art, thus represent a significant negative to their use. Indeed, the application of color in foundation compositions may appear artificial and evident to others. Obviously, the less apparent the beauty aid, the more effective it is.

The removal of color from cosmetic foundation compositions would therefore overcome many of the problems associated with the foundation compositions of the prior art. However, color is essential in providing many of the desirable features of a foundation composition. Color evens skin tone and texture. It also hides skin pores and imperfections. Thus, a new foundation composition which overcomes the problems long associated with foundation compositions of the prior art but which still provides the desirable features of foundation compositions of the prior art would represent a significant advance in the cosmetic art.

2. Background of the Prior Art

Many foundation compositions are described in the prior art. These compositions provide advantages over earlier foundation compositions but require colorants in providing their advantageous effect.

U.S. Pat. No. 3,444,291 discloses a method of filling and camouflaging skin cavities by applying a composition which includes 65 to 75 parts by weight of a microcrystalline wax and about 25 to 35 parts of a mineral oil. The composition includes a colorant, preferably a coal tar dye, for example, D & C Red No. 17, which matches the color of the user's skin.

A spreadable, flowable and greaseless cosmetic coverup composition is taught in U.S. Pat. No. 4,486,405. That composition is characterized by the presence of a first and a second alkoxylated surfactant present in substantially the same concentration. Although the '405 patent composition, unlike earlier foundation compositions, represents an advance over earlier foundation compositions, it shares the disadvantageous property of including a heavy concentration of cosmetically acceptable water insoluble pigments.

U.S. Pat. No. 4,804,532 recites a facial cosmetic powder which utilizes crystalline silica in much lower concentration than that employed in the then prior art compositions. This powder, used as a blush or a facial coating, is said to be effective in hiding skin wrinkles, lines and pores. The composition is a mixture of a color phase and a diluent phase. The color phase is formed by blending crystalline silica with colorants. The resultant color phase is mixed with the diluent phase, essentially formed from nacreous materials such as talc and mica, to form the composition.

The use of a foundation composition which has a significantly high concentration of nacreous material is taught in U.S. Pat. No. 3,978,207. This foundation, a pressed powder composition, is characterized by the presence of a nacreous material such as mica and a binder oil which provides a frosted pearl effect, that is, a lustrous look. The color of this foundation is provided by the nacreous material.

U.S. Pat. No. 4,403,963 describes a foundation composition useful in making up a mannequin. The composition comprises a polymeric film-forming material, a water-insoluble white powder. The powder, which has an average particle size of from 2 to 100 microns, represents 20 to 60 weight percent of the composition. This composition is recited to overcome the problems associated with making up a mannequin using conventional makeup material. Conventional foundation compositions, designed for use on human skin, do not adhere to nor uniformly spread onto the surface layer of a synthetic resin of a mannequin.

U.S. Pat. No. 4,407,789 sets forth a high moisture absorbent body powder composition. The composition comprises finely divided rice hulls which passes through a 200 mesh sieve. Finely divided rice hulls are recited to possess far better water absorption than talc, the principal ingredient usually employed in body powders. Although this composition does not include a colorant, this product is not a foundation composition. Rather, it is a dusting powder applied over a foundation composition.

U.S. Pat. No. 4,659,562 discloses a cosmetic makeup composition which includes, as a binding agent therefor, an intimate mixture of from 5 to 95 weight percent of a mixture of finely divided silica and about 5 to 95 weight percent of finely divided polyethylene fibers. The composition is recited to maintain its uniformity over the areas of the skin to which it is applied. That is, it is said to be "creaseproof." The composition of the '562 patent includes colorant albeit in admixture with nacreous agents.

Nakamura et al., Preprints of the XIVth I.F.S.C.C. Congress, Barcelona, 1986, Vol. I, 51–63 (1986) describes a novel makeup composition utilizing spherical silica and polydimethyl siloxane. This combination is recited to provide a foundation which reduces wrinkle visibility to a greater extent than makeup foundations with which it was compared. This reduction in wrinkle visibility is caused by optical blurring enhanced by the novel use of spherical silica and polydimethyl siloxane.

BRIEF SUMMARY OF THE INVENTION

A new invisible foundation composition has now been developed which provides smooth skin tone and texture and blurs fine skin lines, pores and imperfections without the inclusion of a colorant. This foundation composition is also characterized by the absence of the unpleasant feel associated with foundation compositions of the prior art. With these desirable properties come the additional advantage provided by the substantially invisible nature of this composition, making it seem as if the user had not applied any makeup to the skin.

In accordance with the present invention, an invisible foundation composition is provided. The composition comprises a light scattering agent, said agent characterized by a spherical shape with a diameter of up to about 30 microns.

DETAILED DESCRIPTION

The cosmetic foundation composition of the present invention includes a light scattering component. The light scattering agent is characterized by a spherical shape with a diameter of up to about 30 microns. Unlike the inorganic materials utilized in cosmetic compositions of the prior art, such as silica, hydrated silica and silica silylate, among others, as defined the CTFA Cosmetic Ingredient Dictionary, 3rd Ed, Cosmetic Toiletry and Fragrance Assn., Inc., Washington D.C., 1982 incorporated herein by reference, the light scattering agent of the foundation composition is characterized by a spherical shape and a diameter of up to about 30 microns. The inorganic cosmetically acceptable components of the prior art, as defined in the CTFA Cosmetic Ingredient Dictionary, are not spherical. They may be irregularly shaped or may be characterized as platelets, rods or other geometric shapes. What they are not are spherically shaped.

The light scattering agent is preferably a spherical shaped inorganic material having a particle size in the range of between about 3 and about 15 microns. A particularly preferred embodiment of a material meeting these criteria is spherical silica. This material has been recently developed and is not yet included in the aforementioned CTFA Cosmetic Ingredient Dictionary, Third Ed.

Spherically shaped light scattering agents utilized in the foundation composition of this invention are surprisingly effective in hiding skin defects. When the light scattering agent, for example, spherical silica, is present in sufficient concentration, there is less need for including colorants, pigments or the like to hide undesirable skin features.

To provide an invisible foundation composition, that is, a foundation composition free of any colorant, the light scattering agent, preferably spherical silica, is present in a concentration in the range of between about 1.5% and about 30% by weight, based upon the total weight of the foundation composition. More preferably, the light scattering agent constituent of the foundation composition is included in the range of between about 1.75% and about 15% by weight, based on of the total weight of the foundation composition. Still more preferably, the light scattering agent is present in an amount such that it comprises between about 1.9% and about 5% by weight, based on the total weight of the composition.

Although not absolutely essential, it is preferred that the foundation composition include at least one matte finishing agent. A matte finishing agent supplements the skin defect hiding effect of the essential light scattering agent. Thus, the concentration of the matte finishing agent is generally inversely proportional to the concentration of the light scattering agent component in the foundation composition. That is, as a general rule, the greater the concentration of the light scattering agent the less the concentration of the matte finishing agent.

In the preferred embodiment wherein at least one matte finishing agent is present in the foundation composition, that component comprises between about 5% and about 35% by weight, based on the total weight of the composition. Preferably, the matte finishing agent is present in the foundation composition in a concentration of between about 10% and about 30% by weight. More preferably, the matte finishing agent represents between about 15% and about 20% by weight of the foundation composition.

The function of the matte finishing agent, like that of the light scattering agent, which it supplements in the foundation composition, is to hide skin defects. Such cosmetically acceptable inorganic agents, i.e., those included in the CTFA Cosmetic Ingredient Dictionary, Third Ed., as silica, hydrated silica, mica, talc, polyethylene, titanium dioxide, bentonite, hectorite, kaolin, chalk, diatomaceous earth, attapulgite and the like may be utilized. Of particular usefulness as a matte finishing agent is low lustre pigment, a recently developed cosmetically acceptable agent, which is a titanated mica (mica coated with titanium dioxide) coated with barium sulfate. Of the inorganic components useful as a matte finishing agent low lustre pigment, talc, polyethylene, hydrated silica, kaolin, titanium dioxide and mixtures thereof are particularly preferred. Of those particular preferred matte finishing agents low lustre pigment is the agent of choice.

The effectiveness of the light scattering agent with or without one or more matte finishing agents, unlike a teaching of the prior art, eliminates the need of including a silicone oil or the like to insure blurring of skin defects. The unique foundation composition, because of the effective use of its constituents, does not require the inclusion of a silicone oil, such as polydimethyl siloxane, or for that matter any animal, vegetable, or mineral oil.

A third functional component preferably employed in the foundation composition is one or more moisturizing agents. Among the moisturizing agents useful in the foundation composition are such well known cosmetically effective moisturizing agents as glycerin, propylene glycol, hydrogen starch hydrolysate, sorbitol, butylene glycol, hydrolyzed silk, chitin extract and mixtures thereof. All of these agents except chitin extract are defined in the aforementioned CTFA Cosmetic Ingredient Dictionary, Third Ed., incorporated herein by reference. Of these moisturizing agents, glycerin, butylene glycol, hydrolyzed silk, chitin extract and mixtures thereof are particularly preferred for use as the moisturizing agent.

The moisturizing agent, provided by one or more of the aforementioned moisturizing components, in a preferred embodiment is present in a concentration in a range of between about 5% and about 35% by weight, based on the total weight of the composition. More preferably, the moisturizing agent constituent comprises about 7.5% to about 30% by weight of the foundation composition. Still more preferably, the moisturizing agent is present in the foundation composition in a concentration in the range of between about 15% and about 25% by weight.

A third preferred component of the foundation is water. The water constituent, if present, comprises up to about 68% by weight of the foundation composition. Preferably, the water component is present in a concentration of about 10% to about 60% by weight. More preferably, the water constituent in the foundation composition is in the range of between about 20% and about 40% by weight.

In addition to the essential inclusion of a light scattering agent and the preferred inclusion of at least one matte finishing agent, at least one moisturizing agent and water, other components preferably included in the foundation composition include skin conditioning agents.

The skin conditioning agents present in the foundation composition constitute about 6% to about 24% by weight, based on the total weight of the foundation composition. More preferably, the skin conditioning agents comprise between about 8% and about 20% by weight. Still more preferably, skin conditioning agents are present in the foundation composition in a concentration in the range of between about 10% and about 18% by weight. Most preferably, skin conditioning agents represent between about 12% and about 16% by weight of the foundation composition.

Among the cosmetically acceptable skin conditioning agents within the contemplation of the foundation composition of this invention are cetyl octanoate, cetyl acetate, squalane, trioctyl citrate, PEG isoceteth-3 acetate and mixtures thereof. All of these skin conditioning agents, except PEG isoceteth-3 acetate, which will be included in the next edition, are defined in the CTFA Ingredient Dictionary, 3rd Ed., incorporated herein by reference.

Another optional but preferred component of the foundation composition is one or more ultraviolet absorbing agents. Ultraviolet absorbing agents, often described as sunscreening agents, are present in a concentration in the range of between about 1% and about 10% by weight, based on the total weight of the foundation composition. Preferably, the UV absorbing agents constitute between about 2% and about 8% by weight. More preferably, the UV absorbing agents are present in the foundation composition in a concentration range of between about 4% and about 6% by weight. Of the ultraviolet absorbing agents within the contemplation of the foundation composition benzophenone-3, octyl dimethyl PABA (Padimate O) and mixtures thereof are particularly preferred.

A further component optionally included in the foundation composition is a thickening agent. One or more thickening agents are optionally present in the foundation composition in a concentration in the range of between about 0.1% and about 1% by weight, based on the total weight of the foundation composition. Preferably, the thickening agent is present in the foundation composition in a concentration in the range of between about 0.2% and about 0.6% by weight. More preferably, the thickening agent constituent of the foundation composition constitutes between about 0.3% and about 0.5% by weight. A particularly preferred thickening agent utilizable in the foundation composition is xanthan gum.

A chelating agent may also be incorporated in the foundation composition. A chelating agent is preferably present in the foundation composition in a concentration in the range of between about 0.02% to about 0.10% by weight, based on the total weight of the foundation composition. Preferably, the chelating agent is present in a concentration in the range of between about 0.03% and about 0.07% by weight, based on the total weight if the foundation composition. Among the chelating agents that may be included in the foundation composition is trisodium EDTA.

Another optional but preferably included component of the foundation composition is one or more preservatives. The preservative concentration in the foundation composition, based on the total weight of that composition, is in the range of between about 0.2% and about 0.8% by weight, preferably between about 0.4% and about 0.6% by weight. Preservatives within the contemplation of the foundation composition include diazolidinyl urea, methylparaben and ethylparaben. Preferably, the foundation composition includes a mixture of these preservatives.

Yet another optional but preferred component of the foundation composition is one or more emulsifying agents. Emulsifying agents, if present in the foundation composition, are present in a concentration in the range of between about 1% by weight and about 10% by weight. Preferably, the emulsifying agent constituent of the foundation composition comprises between about 2% and about 7% by weight. Most preferably, the emulsifying agent or agents is included in the foundation composition in a concentration in the range of between about 2.5% and about 5% by weight.

An emulsifying agent that may be utilized in the foundation composition is propylene glycol isoceteth-3, a component that will be included in the next edition of the CTFA Cosmetic Dictionary, but is not included in the aforementioned Third Edition. Another preferred emulsifier is Polysorbate 80, defined in said CTFA Cosmetic Dictionary, 3rd Edition.

Other optionally included constituents that may be included in the foundation composition are fragrances and colorants. It is emphasized that the colorant or colorants contemplated for use in the foundation composition is one present in very low concentration. That colorant is included in order to provide the foundation composition with a pleasing appearance in the container in which it is marketed. It is emphasized that the colorant concentration, if present at all, is so low as to impart no color to the skin on which the foundation composition is applied.

A preferred foundation composition comprises between about 32% and about 35% water; between about 8% and about 12% talc; between about 8% and about 12% glycerin; between about 6% and about 10% butylene glycol; between about 4% and about 8% trioctyl citrate; between about 4% and about 8% polyethylene; between about 3% and about 7% cetyl octanoate; between about 1% and about 5% propylene glycol isoceteth-3 acetate; between about 1.5% and about 5% spherical silica; between about 1% and about 3% squalane; between about 1% and about 2% hydrated silica; between about 0.5% and about 1.5% of a mixture of Polysorbate 80, acetylated lanolin alcohol and cetyl acetate; between about 0.5% and about 1.5% kaolin; between about 0.25% and about 0.75% hydrogenated silk; between about 0.4% and about 0.8% xanthan gum; between about 1% and about 3% low lustre pigment; between about 0.25% and about 1% benzophenone-3; between about 1.5% and about 4.5% octyl dimethyl PABA; between about 1.5% and about 4.5% chitin extract; between about 0.025% and about 0.075% trisodium EDTA; between about 0.1% and about 0.3% methylparaben; between about 0.1% and about 0.2% ethylparaben; between about 0.1% and about 0.2% diazolidinyl urea; and between about 0.05% and about 0.15% titanium dioxide, wherein all the percentages are by weight based on the total weight of the foundation composition.

In addition to the about recited constituents present in the concentration ranges reported above, a fragrance, geranium extract dissolved in dipropylene glycol, is preferably present in the above foundation composition in a concentration of between about 0.05% and about 0.2%. Also, one or more colorants present in a concentration sufficient to provide a pleasing color to the composition in the container in which it is sold may be included. A minute concentration of the colorant iron oxides, particularly iron oxide red and/or iron oxide yellow, is preferably employed to provide this function.

The following example is given to illustrate the scope of the foundation composition of the present invention. Because this example is given for illustrative purposes only, the invention should not be limited thereto.

EXAMPLE

Preparation of a Foundation Composition

A first agitator equipped, jacketed kettle was charged with 29.15 parts (parts by weight) water, 10 parts glycerin, 4 parts butylene glycol, 0.05 part trisodium EDTA and 0.15 part diazolidinyl urea. The combined contents of the first kettle was agitated until a clear and homogenous solution was obtained.

A first mixing container equipped with an agitator was charged with 4 parts butylene glycol. To this was added 0.2 part methylparaben and 0.15 part ethylparaben. These ingredients were mixed until a uniform and clear liquid was obtained. To this clear liquid was added 0.6 part xanthan gum. The resultant product was agitated until a lump-free slurry was obtained. The contents of the first mixing container was then transferred to the first jacketed kettle.

The contents of the first kettle, including the newly added contents of the first mixing container, was agitated for 30 minutes whereupon a thick homogeneous liquid was formed. To this homogeneous liquid was added 1 part of a mixture of Polysorbate 80, acetylated lanolin alcohol and cetyl acetate. Again, the resultant contents of the first kettle was mixed under agitation until a uniform bulk product was obtained. Thereupon 1.5 parts hydrated silica, 2 parts of spherical silica, 0.1 part titanium dioxide, 1 part kaolin, 10 parts talc, and 0.005 part iron oxide red was added to the first kettle in the sequence recited above. The combined contents of the first kettle was agitated and mixed at a temperature of between 82° F. and 90° F. Upon the obtaining of a uniform mixture, 0.5 part hydrolized silk and 3 parts chitin extract were added to the agitated mixture After all the ingredients in the first kettle were dispersed, the contents were transferred to a second agitator equipped jacketed kettle including water rinsings which added 5 parts of water to the composition.

Three parts propylene glycol isoceteth-3 acetate, 6 parts trioctyl citrate, 5 parts cetyl octanoate, 2 parts squalane, 3 parts octyl dimethyl PABA, 0.5 part benzophenone-3 and 0.1 part geranium extract dissolved in dipropylene glycol were thereafter charged into a second mixing container equipped with an agitator. The components introduced into the second container were vigorously mixed until no solids remained in the mixture. Thereupon, 6 parts polyethylene and 2 parts low lustre pigment (barium sulfate coated titanated mica) were added slowly to the mixture. Mixing continued until the two solids were uniformly suspended therein.

The contents of the uniformly suspended mixture in the second mixing container were transferred into the second kettle while the kettle was agitated. When a smooth and uniform product was obtained the product, the foundation composition, was removed from the kettle.

The above preferred embodiments and examples are given to illustrate the scope and spirit of the present invention. These embodiments and examples will make apparent, to those skilled in the art, other preferred embodiments and examples. These other preferred embodiments and examples are within the contemplation of the present invention. Therefore, the present invention should be limited only by the appended claims.

What is claimed is:

1. A foundation composition comprising a light scattering agent, which agent is a spherically shaped inorganic material having a diameter of up to about 30 microns; a matte finishing agent, a moisturizing agent, and water.

2. A composition in accordance with claim 1 wherein said light scattering agent is spherical silica.

3. A composition in accordance with claim 1 wherein said matte finishing agent is selected from the group consisting of low lustre pigment, kaolin, hydrated silica, titanium dioxide, talc, mica, polyethylene, silica, chalk, calcium oxide, diatomaceous earth, alumina, bentonite, hectorite, attapulgite and mixtures thereof.

4. A composition in accordance with claim 3 wherein said matte finishing agent is selected from the group consisting of low lustre pigment, kaolin, hydrated silica, titanium dioxide, talc, polyethylene and mixtures thereof.

5. A composition in accordance with claim 4 wherein said matte finishing agent is a low lustre pigment selected from the group consisting of titanated mica coated with barium sulfate, talc, polyethylene, hydrated silica, kaolin, titanium dioxide, or mixtures thereof.

6. A foundation composition comprising from about 1.5% to about 30% of a light scattering agent having a spherical shape and a diameter of up to about 30 microns; from about 5% to about 35% of a matte finishing agent; from about 5% to about 35% of a moisturizing agent; and up to about 68% water, all said percentages being by weight based on the total weight of the composition.

7. A composition in accordance with claim 6 wherein said light scattering agent represents between about 1.9% and about 5%; said matte finishing agent represents between about 15% and about 20%; and said moisturizing agent comprises between about 15% and about 20%.

* * * * *